(12) United States Patent
Tiknius et al.

(10) Patent No.: US 9,079,157 B2
(45) Date of Patent: Jul. 14, 2015

(54) PROTEIN REMOVAL AGENT

(71) Applicants: Vitalis Tiknius, Vilnius (LT); Eglé Merkiene, Vilnius (LT)

(72) Inventors: Vitalis Tiknius, Vilnius (LT); Eglé Merkiene, Vilnius (LT)

(73) Assignee: Thermo Fisher Scientific Baltics, UAB, Vilnius (LT)

( * ) Notice: Subject to any disclaimer, the term of this patent is extended or adjusted under 35 U.S.C. 154(b) by 0 days.

(21) Appl. No.: 13/953,263

(22) Filed: Jul. 29, 2013

(65) Prior Publication Data

US 2014/0093937 A1    Apr. 3, 2014

(30) Foreign Application Priority Data

Sep. 28, 2012 (GB) .................................. 1217405.8

(51) Int. Cl.
*C12N 9/99* (2006.01)
*C12N 15/10* (2006.01)
*B01J 20/22* (2006.01)

(52) U.S. Cl.
CPC .................. *B01J 20/223* (2013.01); *C12N 9/99* (2013.01); *C12N 15/1003* (2013.01); *C12N 15/1006* (2013.01)

(58) Field of Classification Search
None
See application file for complete search history.

(56) References Cited

U.S. PATENT DOCUMENTS

| | | | |
|---|---|---|---|
| 3,053,782 A * | 9/1962 | Shelby | 524/600 |
| 4,894,468 A | 1/1990 | Wilchek et al. | |
| 4,923,978 A | 5/1990 | McCormick | |
| 5,625,055 A | 4/1997 | Caddy et al. | |
| 7,067,298 B2 | 6/2006 | Latham et al. | |
| 7,115,719 B2 | 10/2006 | Paulsen | |
| 7,264,932 B2 | 9/2007 | Latham et al. | |
| 2005/0059054 A1 | 3/2005 | Conrad et al. | |
| 2009/0175765 A1 | 7/2009 | Harris et al. | |

FOREIGN PATENT DOCUMENTS

| | | |
|---|---|---|
| EP | 0 771 870 | 5/1997 |
| EP | 1 078 984 | 2/2001 |
| EP | 1135479 B1 | 12/2002 |
| EP | 1 674 570 | 6/2006 |
| EP | 1 806 400 | 7/2007 |
| WO | 92/05181 | 4/1992 |
| WO | 92/05181 A1 | 4/1992 |
| WO | 98/31840 | 7/1998 |
| WO | 98/31840 A1 | 7/1998 |
| WO | 00/33826 | 6/2000 |
| WO | 02/38758 | 5/2002 |
| WO | 02/38758 A1 | 5/2002 |
| WO | 02/102879 | 12/2002 |
| WO | 02/102879 A2 | 12/2002 |
| WO | 2005/054466 | 6/2005 |

OTHER PUBLICATIONS

Chen et al. "Preparation and characterization of polyester/silica nanocomposite resins" Progress in Organic Coatings 54 (2005) 120-126.*
Gibaud et al. "Influence of functional organic groups on the structure of CTAB templated organosilica thin films" J.Mater Chem 2004 14 1854-1860.*
Moran et al. "Synthesis and characterization of lanthanide-doped silica microspheres" Langmuir 2001 17, 8376-8379.*
United Kingdom Search Report, GB1217405.8 mailed Jan. 25, 2013 (4 pages).
Applied Biosystems, Turbo DNA-free™ Kit. (Apr. 2009), 12 pages.
Agilent Technologies, StrataClean Resin Instruction Manual (2009), 11 pages.
Clontech, QuickClean™ Enzyme Removal Resin Brochure (3 pages) and Protocol-at-a-Glance (1 page), 2009.
Liu et al. A rapid method for the purification of the methanol dehydrogenase from *Methylobacterium exotorquens*. Protein Expr. Purif. vol. 46 (2006), pp. 316-320.
Kirby. A New Method for the Isolation of Deoxyribonucleic Acids: Evidence on the Nature of Bonds between Deoxyribonucleic Acid and Protein. Biochem. J. 66: 495-504 (1957).
Marmur. A Procedure for the Isolation of Deoxyribonucleic Acid from Micro-organisms. J. Mol. Biol. 3: 208-218 (1961).
Marko et al. A Procedure for the Large-Scale Isolation of Highly Purified Plasmid DNA Using Alkaline Extraction and Binding to Glass Powder. Anal. Biochem. 121(2): 382-387 (1982).
Boom et al. Rapid and Simple Method for Purification of Nucleic Acids. J. Clinical. Microbiology. 28(3): 495-503 (1990).
Chen and Liao. Structure and Function of Bovine Pancreatic Deoxyribonuclease I. Protein Peptide Lett. 13: 447-453 (2006).
Huang et al. Optimization of Dnase I Removal of Contaminating DNA from RNA for Use in Quantitative RNA-PCR. BioTechniques 20: 1012-1020 (1996).
Silkie et al. Reagent decontamination to eliminate false-positives in *Escherichia coli* qPCR. J.Microbiol. Meth. 72: 275-282 (2008).
McCormick. A Solid-Phase Extraction Procedure for DNA Purification. Analyt. Biochem. 181: 66-74 (1989).

(Continued)

*Primary Examiner* — Suzanne M Noakes
*Assistant Examiner* — Gerard Lacourciere
(74) *Attorney, Agent, or Firm* — Thompson Hine LLP

(57) ABSTRACT

The present invention provides compositions, methods and kits for the removal of proteins from complex reaction mixtures useful in majority workflows of molecular biology research experiments. More specifically, such compositions, methods and kits are useful in such processes as purification of nucleic acids from biological samples or after their treatment with specific enzymes, when residual enzyme activity in reaction mixture is not compatible with downstream applications.

21 Claims, 9 Drawing Sheets

(56) References Cited

OTHER PUBLICATIONS

Min et al. Chiral Transformation in Protonated and Deprotonated Adipic Acids through Multistep Internal Proton Transfer. Chem. Eur. J. 16: 10373 (2010).

Erim al. Performance of a physically adsorbed high-molecular-mass polyethyleneimine layer as coating for the separation of basic proteins and peptides by capillary electrophoresis. Journal of Chromatography A. (1995) 708(2):356-361.

Evtushenko. Protein-Binding Matrices for Phenol-free Extraction of DNA and RNA Modifying Enzymes: Applications for High Throughput Sample Processing [M-34]. Research Institute of Roentgenology and Radiology, St. Petersburg, Russia. BT$i$ (2000), 12(2): 3 pages.

Blackburn, et al. Ribonuclease inhibitor from human placenta: interaction with derivatives of ribonuclease A. J. Biol. Chem. 1979, 254:12488-12493.

Bickler, et al. Magnesium-Dependent Thermostability of DNase I. 5 pages article in BioTechniques. vol. 13, No. I Jul. 1992.

Extended European Search Report, EP13186688.1-1406, mailed Jan. 29, 2014, 9 pages.

Falipou et al. New Use of Cyanosilane Coupling Agent for Direct Binding of Antibodies to Silica Supports. Physicochemical Characterization of Molecularly Bioengineered Layers. Bioconjugate Chemistry, 10 (1999) 346-353.

Palacián et al. Dicarboxylic acid anhydrides as dissociating agents of protein-containing structures, Molecular and Cellular Biochemistry, 97 (1990) 101-111.

* cited by examiner

PROTEIN REMOVAL AGENT

This application claims priority to Great Britain Application Serial No. 1217405.8, filed Sep. 28, 2012, the entirety of which is incorporated by reference herein in its entirety.

The invention provides compositions, methods and kits for the removal of proteins from complex reaction mixtures useful in majority workflows of molecular biology research experiments. Such compositions, methods and kits are useful in processes such as purification of nucleic acids from biological samples or after their treatment with specific enzymes, when residual enzyme activity in reaction mixture is not compatible with downstream applications.

Purification of nucleic acids from solutions containing enzymes acting on the nucleic acids and/or other proteinaceous materials is a frequently performed operation in life science research. Removal of enzymes used in the preceding manipulation stage from nucleic acids solutions is almost always required before downstream processing.

There are many methods for protein/enzyme removal from reaction mixtures known in the art. The main parameters important for the user of such methods are complete inactivation of any enzyme and denaturation/removal of all proteins from reaction mixture, good yields of nucleic acids, convenience of use, and absence of hazardous materials and safety concerns.

One of the first methods used for protein removal from biological solutions/reaction mixtures was liquid partitioning method using organic solvents. This method described by Kirby (Biochem. J. 66: 495-504 (1957) and Marmur (J. Mol. Biol. 3: 208-218 (1961)), with many later modifications, uses the difference of partition behavior of nucleic acids and proteins in organic/water two phase systems, where proteins move to the organic phase and nucleic acids are collected from the aqueous phase. The aqueous solution of nucleic acids is usually sequentially partitioned in phenol/water and in chloroform/water biphasic systems.

Despite high efficiency of protein removal, this method has disadvantages. It is labor- and time-consuming. It is a deemed health hazard because the organic compounds used are flammable, corrosive, toxic, irritant and carcinogenic. It is a deemed environmental hazard because large volumes of non-biodegradable compounds are used. Additional manipulation steps are required to remove organic compounds: washing aqueous phase with diethyl ether, precipitating nucleic acids with ethanol/acetate, dialysis, etc.; these are time consuming and may result in some nucleic acid loss and thus lower yields.

Another known method of protein/nucleic acids separation is based on an adsorption/elution cycle on solid support. This method (Marko et al., Anal. Biochem. 121 (1982) 382 and later modified by Boom et al. J. Clin. Microbiol. 28 (1990) 495) uses the property of nucleic acids to bind to silica, e.g., glass milk, glass fibers, diatomaceous earth, particulate and membranous silica, zeolites, etc., in the presence of alcohol and either chaotropic or kosmotropic (Invitek GmbH EP 1135479B1) agents.

This procedure is usually embodied in the form of spin-column purification where the solid phase active substance, silica, is packed into a small column through which the flow of liquid phase is achieved by applying centrifugal force. A series of binding, washing and elution steps is applied.

This method is more convenient for the user because no irritant and foul-smelling substances are required, and reagents are used in lower quantities, are less hazardous, and are more environment-friendly. However, this method has the following disadvantages: it consists of multiple manipulations and centrifugation steps that require centrifugation equipment compatible with spin column format, the comparatively low selectivity of silica requires the use of column technology, the yield of nucleic acids is limited by the adsorption capacity of silica layer as well as by the dead volume of the same layer, it uses a multistep procedure requiring time and skilled labor, and certain impurities, e.g., RNases, may survive the procedure and may be detrimental to downstream applications.

Another widely used method of protein elimination from reaction mixtures is enzyme inactivation by heat. This method is simple and is applicable if the only substance interfering with downstream workflow is the active form of the enzyme. Enzyme classes that are most often eliminated from reaction mixtures by heat inactivation are deoxyribonucleases (non-specific deoxyribonucleases and restriction enzymes). The most frequently used non-specific nuclease is pancreatic DNase I which is easily inactivated by heat. However, $Ca^{2+}$ and $Mg^{2+}$ ions, when available, interfere with thermoinactivation (Chen and Liao, Protein Peptide Lett. 13: (2006) 447), and addition of chelates is required before heat treatment (Huang et al., BioTechniques 20 (1996) 1012; Silkie et al., J. Microbiol. Meth. 72 (2008) 275). However, even thermoinactivated DNase I will partially regain its activity during downstream procedures after contact with $Ca^{2+}$ or $Mg^{2+}$ ions (Bickler et al., BioTechniques 13 (1992) 64). If the nucleic acid to be purified was RNA, it will be degraded by heat as well, although less if chelators and reducing agents were present in solution, and the thermoinactivation conditions must be thoroughly optimized to maximize the yield of RNA (Huang et al., op. cit.]. There are many deoxyribonucleases (both non-specific and restriction enzymes) that are very resistant to elevated temperatures. Most ribonucleases are impossible to inactivate by heat at all, and many enzymes regain their activity after thermoinactivation.

Although heat inactivation has advantages of convenience, speed, and simplicity, it has the following disadvantages: it is suitable only for certain contaminating proteins, e.g., for DNase I; it does not physically separate contaminating protein species from the working solutions comprising nucleic acids, but only stops or substantially reduces enzymatic activity; it may cause deleterious side effects, e.g., reactivation of thermoinactivated enzymes, degradation of target nucleic acid, and various physical and chemical processes such as depurinization of DNA, formation of precipitates etc.; and enzyme inactivation is partially reversible.

Another method for removal of undesirable enzymatic activity from reaction mixtures is inactivation of enzymes by chemical substances leaving the inactive species physically in the solution. However, the majority of chemical substances that inactivate enzymes exhibit low specificity towards specific enzymatic activity, and thus the reaction mixture must be re-purified prior to performing subsequent reactions. These substances also often modify not only enzymes but nucleic acids as well, e.g. diethyl pyrocarbonate modifies adenine residues. The notable exception is mammalian ribonuclease inhibitor protein (Blackburn et al., J. Biol. Chem. 252 (1977) 12488) which inhibits ribonucleases from RNase A class.

The above described method has the advantage of convenience, speed and simplicity, but has the following disadvantages: it is suitable only for certain contaminating materials, e.g., placental RNase inhibitor used for RNase A; it does not physically separate contaminating species from the reaction mixture but only stops their action; it introduces foreign chemical substances that must be purified from the reaction mixture before downstream workflow; chemical substance may display deleterious activity against nucleic acids; and some substances, e.g., diethyl pyrocarbonate, are toxic, irritant, carcinogenic, etc.

Several suppliers offer commercial products for enzyme/protein removal from reaction mixtures based on the principle of impurities adsorption onto a solid support, leaving nucleic acids in the liquid phase. This class of methods (McCormick, Analyt. Biochem. 181 (1989) 66; U.S. Pat. Nos. 4,923,978; 7,264,932; QuickClean reagent (Clontech) exploits a very simple solid-phase extraction procedure enabled by the extremely strong interaction between specialty adsorbents and proteins to be removed. In McCormick, a phenol silica is prepared for this purpose. In contrast, U.S. Pat. No. 4,923,978 describes a different process for purifying nucleic acids. A solid phase extraction material is prepared from a commercially available silica by removing polyvalent cationic material from the surface thereof. This is achieved by acid washing to produce a pure native silica surface layer to prevent nucleic acid adsorption thereto. This solid phase was able to bind enzymes with sufficient strength even in static conditions without significant binding of nucleic acids.

The main disadvantages characteristic for this class of methods are: the adsorbent must be thoroughly designed for a given enzyme; residual activities of enzymes after removal may be still high enough to interfere with downstream workflow; non-specific nucleic acid sorption onto solid support may negatively affect its yield after treatment; and the method is more prone to user error than most alternatives.

A need thus exists for efficient universal protein removal from reaction mixtures reagent that exhibit the following characteristics: residual enzyme activity after their removal is sufficiently low to avoid interference with downstream workflow; nucleic acid yields are almost the same before and after treatment with the reagent; the reagent is convenient to use; and the reagent is free from hazardous materials and has no safety concerns. Such method must be quick and simple, and capable of total removal of enzymes from various reaction mixtures leaving nucleic acids in biologically active state without introducing foreign compounds interfering with downstream procedures.

In a first aspect, the invention provides use of a solid phase having a surface that comprises a functionalized silica for removal of protein contaminants from a solution containing target nucleic acid, where the functionalized silica bears anionic or neutral substituent groups that are (i) polar, other than phenyl, and/or (ii) comprise a $C_1$ to $C_3$ alkyl chain.

The invention provides an improved and simplified method and composition for removal of protein contaminants from solutions containing useful, i.e., target, nucleic acids. These solutions may be complex mixtures originating from biological samples in the workflow of nucleic acids sample preparation for further analysis using well known methods such as PCR, qPCR, cloning, or next generation sequencing workflow. The solid phase may be used for removal of protein contaminants such as nucleic acid enzymes. These may be enzymes acting on nucleic acids, such as DNA/RNA polymerases, non-specific deoxy- and ribonucleases such as DNase I, restriction endonucleases, RNase A, etc., phosphatases, ligases from reaction mixtures in routine laboratory workflow prior to transferring nucleic acid into the next reaction step. The protein removal effect in the present invention is achieved by the solid phase.

The surface of the solid-phase comprises a functionalized silica that may be present as a coating on a substrate which is a non-silica substrate, or the entire solid phase may comprise silica. The solid phase has at its surface substituent groups that may be polar substituent groups and/or weakly hydrophobic substituent groups. The substituent groups may be anionic or neutral substituent groups that are (i) polar, other than phenyl, and/or (ii) comprise a $C_1$ to $C_3$ alkyl chain. Polar neutral substituent groups are typically dipoles, which may be immobilized to the solid phase by short hydrophobic handles that typically comprise $C_1$ to $C_3$ alkyl chain. Anionic substituent groups include sulfonate or alkanoyl groups that may be immobilized to the solid phase by a hydrophobic handle such as $C_1$ to $C_3$ alkyl chain.

The absence of cationic substituent groups and phenolic substituent groups inhibits or prevents nucleic acid binding to the solid phase, which is undesirable and may lead to reduced nucleic acid yields when the solid phase is used.

In one embodiment the substituent groups are selected from cyanoalkyl groups ($CN$—$(CH_2)_n$—) where n is an integer that is at least 3; short chain alkyl groups ($CH_3$—$(CH_2)_m$—) where m is 0, 1 or 2; sulfoalkyl groups ($HSO_3$—$(CH_2)_l$—) where l is an integer in the range 2 to 6, alkanoyl groups ($CH_3$—$(CH_3)_p$—$CO$—$O$—) where p is 0, 1 or 2; or a diol (($OH)_2$—$CH$—$(CH_2)_r$—), or hydroxyl $OH$—$(CH_2)_r$— where r is zero or an integer in the range 1 to 5, or mixed diol $CH_2OH$—$CHOH$—$(CH_2)_t$—; or cyclohexyldiol $C_6H_9(OH)_2$—$(CH_2)_t$—; or alkylhalides $Hal$-$(CH_2)_t$—; or tosylhalides $SO_2Hal$-$C_6H_4$—$(CH_2)_t$—; or tosyl $SO_3H$—$C_6H_4$—$(CH_2)_t$—; or alkylphenylhalides $Hal$-$(CH_2)_u$—$C_6H_4$—$(CH_2)_t$— where Hal is halogen, t is 2, 3, or 4, and u is 0, 1, or 2.

In one embodiment cyanoalkyl groups are cyanopropyl groups. In one embodiment alkanoyl groups are acetyl groups.

The solid phase typically comprises particles that may be approximately spherical and may have a diameter in the range of 3 μm to 15 μm. In one embodiment the particles have pores with a diameter of from 10 nm to 100 nm. Porous silica particles provide a relatively high surface to volume ratio that facilitates binding of the protein contaminants to the particles.

In one embodiment the surface of a solid phase further comprises small substituted silane groups —$O$—$Si$—$R_3$ where R is $C_1$ to $C_3$ alkyl groups or mixture thereof. These groups may be formed by capping any free silanol groups present on the surface of the solid phase, e.g., after the silica surface has been functionalized with the bulky surface substituent groups discussed above. This prevents unwanted nucleic acid binding.

Removal of protein contaminants is carried out in the presence of a poly acid that comprises a polycarboxylic acid, a polyphosphonic acid or a polycarboxylate or a polyphosphonate salt. As further described below, the concerted action of the polyacid anion and the functional groups on the silica surface promotes the irreversible adsorption of the protein contaminants onto the solid phase.

The polycarboxylic acid has two or more carboxylate groups. The polycarboxylic acids may be saturated or unsaturated and may be aliphatic acids or aromatic acids, or cyclic saturated acids. The polycarboxylic acids may incorporate heteroatoms as part of the carbon chain between carboxylate functions or as substituent groups. The polycarboxylic acids may be substituted or unsubstituted and may be linear or branched chain.

The polycarboxylic acids may be saturated or unsaturated and may be aliphatic acids or aromatic acids, or cyclic saturated acids. The polycarboxylic acids may incorporate heteroatoms as part of the carbon chain between carboxylate functions or as substituent groups. The polycarboxylic acids may be substituted or unsubstituted and may be linear or branched chain.

The polycarboxylic acids may include, but are not limited to, saturated and unsaturated aliphatic acids such as oxalic acid, malonic acid, succinic acid, glutaric acid, adipic acid, pimelic acid, suberic acid, azelaic acid, sebacic acid, maleic acid, fumaric acid, itaconic acid, glutaconic acid, citraconic acid, mesaconic acid and their derivatives, malic acid, tartaric acid, glutamic acid, galactaric acid. Aromatic acids include phthalic acid, isophthalic acid, terephthalic acid. Cyclic saturated acids include camphoric acid. Some other acids may have three or more carboxylate groups or incorporating heteroatoms: tricarballylic acid, trimesic acid and its isomers, mellitic acid and isocitric acid.

In one embodiment the polycarboxylic acid comprises a dicarboxylic acid. The dicarboxylic acid may be aliphatic, and may be unsubstituted. In one embodiment the dicarboxylic acid is COOH—$(CH_2)_q$—COOH where q is in the range of 4 to 6. In one embodiment the dicarboxylic acid is adipic acid or is pimelic acid. In one embodiment the dicarboxylic acid is adipic acid.

As an alternative to the polycarboxylic acids, analogous polyphosphonic acids may be used. Such phosphonic acids are typically analogues of the above polycarboxylic acids such as linear alkane diphosphonic or hydroxyalkane diphosphonic acids. One such acid is etidronic acid, which is a diphosphonic acid.

In one embodiment the polyacid is present at a concentration up to 200 mM. The removal of protein contaminants may be carried out at pH 4.5 to pH 7.0. The presence of the polyacid may act as a buffer within this pH range. pH may suitably be adjusted by an appropriate base such as an alkali metal hydroxide such as sodium hydroxide or potassium hydroxide.

In one embodiment a composition for the removal of protein contaminants from a solution containing target nucleic acid is disclosed. The composition comprises (i) a polyacid, which comprises a polycarboxylic acid, a polyphosphonic acid or a polycarboxylate or polyphosphonate salt; (ii) a solid phase having a surface which comprises a functionalized silica.

The polyacid or salt thereof and the solid-phase are as described herein.

The above composition may be applied directly to a composition containing target nucleic acid and protein contaminants such as nucleic acid enzymes.

In one embodiment, a kit for the removal of protein contaminants from a solution containing target nucleic acid is disclosed. The kit comprises (i) a polyacid, which comprises a polycarboxylic acid, a polyphosphonic acid or a polycarboxylate or polyphosphonate salt; and (ii) a solid phase having a surface which comprises a functionalized silica.

The polyacid or salt thereof and the solid phase may be supplied as separate components in a kit, optionally together with instructions for their use. Each component of the kit may be supplied in separate containers. The kit may comprise further components such as other solutions for use in removal of the protein contaminants.

The polyacid or salt thereof and the solid phase are as described herein.

In one embodiment a nucleic acid reaction kit is disclosed. The nucleic acid reaction kit may comprise a nucleic acid enzyme and a composition for the removal of protein contaminants as described herein. Alternatively, the nucleic acid reaction kit may comprise a nucleic acid enzyme for acting on a target nucleic acid and a solid phase having a surface which comprises a functionalized silica for the removal of the nucleic acid enzyme from a solution containing the target nucleic acid, where the functionalized silica bears anionic or neutral substituent groups which are (i) polar, other than phenol, and/or (ii) comprise a $C_1$ to $C_3$ alkyl chain.

The nucleic acid reaction kit may contain instructions for use. Each component may be supplied in a separate container. The nucleic acid enzyme and the solid-phase are described in further detail herein. This nucleic acid reaction kit may further comprise a polyacid or salt thereof. The polyacid or salt thereof may be supplied in a further container or may be present with the nucleic acid enzyme or the solid phase.

Additional reagents may be included in the protein removal composition, such as conservants, stabilizers, or additional reagents for removal of other components coming from upstream reaction mixtures.

While not limited to a specific theory, it is thought that the interaction between functionalized silica and protein mainly proceeds by mutual attraction of:
a) hydrophobic moieties that include methylene handles of cyanopropyl groups, capping alkyl groups when present on solid phase, and siloxane groups on silica vs. hydrophobic patches on protein molecule; and
b) ionized groups such as negatively charged terminal nitriles of cyanopropyl groups and residual silanols on silica vs. positively charged amino acid residues on protein molecule.

The concerted action of dicarboxylic acid or other diacid anions and functionalized silica promotes the irreversible adsorption of proteinaceous compounds onto the solid phase. For example, molecules of aliphatic dicarboxylic acids, e.g., adipic acid, either in protonated or in deprotonated form, have in solution hydrophobic (containing methylene chain) and hydrophilic (containing carboxyls) halves because of its overall curved structure (Min et al., Chem. Fur. J. 16: 10373 (2010)). This is achieved by intramolecular hydrogen bonding of an OH donor of one carboxyl group to the carbonyl oxygen of another carboxyl group, acting as an acceptor. Additionally, the functional groups immobilized on the porous silica structures disrupt the extensive intermolecular hydrogen bonding network characteristic for the solutions of dicarboxylic acids and favor the formation of intramolecular hydrogen bonding. This way a large fraction of acid molecules acquires considerable dipole momentum and may act as ion-pairing reagents.

This property of diacids such as dicarboxylic acids may allow mutual attraction between sterically isolated, normally non-interacting amino acid residues on the protein surface and active groups on the silica surface by creating the bridges between them.

Larger numbers of interacting amino-acid residues may also destabilize the tertiary structure of an active enzyme. The inventors have found that even if the silica microspheres containing the adsorbed enzyme are not removed by centrifugation, usually no residual or reactivatable enzymatic activity is detected after incubation at conditions favoring reactivation, and this activity does not increase (as in the case of reactivation) in time.

These findings show that the inventive Protein Removal Reagent (PRR) acts not only by enthalpic adsorption processes which include hydrophobic and electrostatic interaction, hydrogen bonding, dipole interactions and van der Waals forces, but by entropic processes too. Hydrophobic groups at silica surface and aliphatic chains of dicarboxylic acids or other diacids disrupt the native hydrogen bond network of water and nearby protein structures, mainly (anti)parallel beta-structures responsible for the shape of native protein molecule. Carboxyl groups of dicarboxylic acids form non-native salt bridges with positively charged protein side chains. These entropic processes are essentially irreversible and result in the decrease of the ordered conformation of bound proteins resulting in disruption of tertiary structures, expulsion of interstitial water, release of counter-ions responsible for maintaining native structure and activity. Both these processes yield inactive unfolded proteins fixed onto the silica surface.

This attraction is much stronger than the chelating action of carboxylic acids alone. Whereas the affinity for divalent ions necessary for activity of most enzymes is by orders of magnitude greater for EDTA, iminodiacetic acid, or nitrilotriacetic acid derivatives, these compounds have much lower efficiency in the composition when used instead of aliphatic dicarboxylic acid.

This attraction is much stronger than an interaction between adsorbents suspended in pure water. Although all tested adsorbents bearing diverse functional groups (sulfopropyl, cyanopropyl, hydroxy, etc.) did display efficiency in enzymes absorption, the efficiency was lower as compared to that characteristic to that of the inventive composition.

Treatment with an inventive composition is more efficient than traditionally employed protein removal methods, such as thermoinactivation of enzymes by heat in the excess of chelating agent (EDTA), or commercially available products for protein removal. Enzymes that are not amenable to heat inactivation, e.g., some restriction endonucleases, are readily removed by the inventive compositions. Residual dicarboxylic acid ions remaining in the reaction mixture after treatment did not interfere with the majority of downstream applications. No chaotropic or other active compounds are used in the inventive (or high concentrations of less active compounds, like salts, detergents or and water-soluble organic materials) unlike in known formulations such as U.S. Pat. No. 7,115,719, thereby making the inventive compositions and methods environmentally safe.

Commercial products for protein removal currently available, such as DNA-free™ Kit (Ambion, McCormick, Analyt. Biochem. 181:66 (1989); DNA-free™ Kit Ambion® Manual #1907M revision F. Jul. 9, 2009) are by orders of magnitude less efficient than the inventive compositions.

Protein removal with a protein removal reagent (PRR) typically involves a) admixing the inventive composition with nucleic acid containing solution, in one embodiment at a ratio 1:10 or ratios dependent on the protein quantity present in the solution, e.g. one µL PRR decreases the activity of 0.5 unit of wild-type DNase I, or *E. coli* RNase I, or various restriction enzymes beyond the detection limit. Protein sorption onto PRR is achieved by mixing the resulting suspension by vortexing for several seconds; b) suspension centrifugation immediately after admixing with PRR and recovery of supernatant containing protein-free nucleic acid solution. The method may be performed at room temperature and does not require additional incubation time for protein binding.

The invention is now described in further detail with reference to the following Examples and related Figures.

EXAMPLE 1

PRR Composition Synergistic Action of Silica Adsorbent and Dicarboxylic Acid Salts Several versions of PRR were prepared by suspending cyanopropyl derivatized silica (50% slurry) either in pure water or in buffer containing dicarboxylic acid salt (Na-adipate or Na-suberate) at pH 5.0. Efficacy of prepared PRR samples was tested as their ability to remove DNase I from reaction mixture. One unit DNase I suspended in 20 µl 1× Reaction Buffer with $MgCl_2$ was treated with 2 µl PRR variant. For comparison, aliquots of the same reaction mixture had been treated with the same volumes of pure Na-adipate or Na-suberate buffer without silica. All samples were centrifuged and 20 µL of supernatant from each sample were transferred to a fresh tube. One µg supercoiled pUC 19 plasmid DNA was added to each tube and incubated for two h at 37° C. to detect residual DNase I activity. In parallel, DNase I activity calibration was performed to allow evaluation of the DNase I amount in sample from extent of pUC 19 DNA degradation. From 1 to $10^{-7}$ units DNase I were added to 1 µg pUC19 DNA in 20 µl 1× Reaction Buffer with $MgCl_2$ and incubated for two h at 37° C. to resemble experimental conditions. All samples were analyzed electrophoretically in 1% agarose gel in TAE buffer and the gel was stained with ethidium bromide to visualize DNA.

Figure 1:
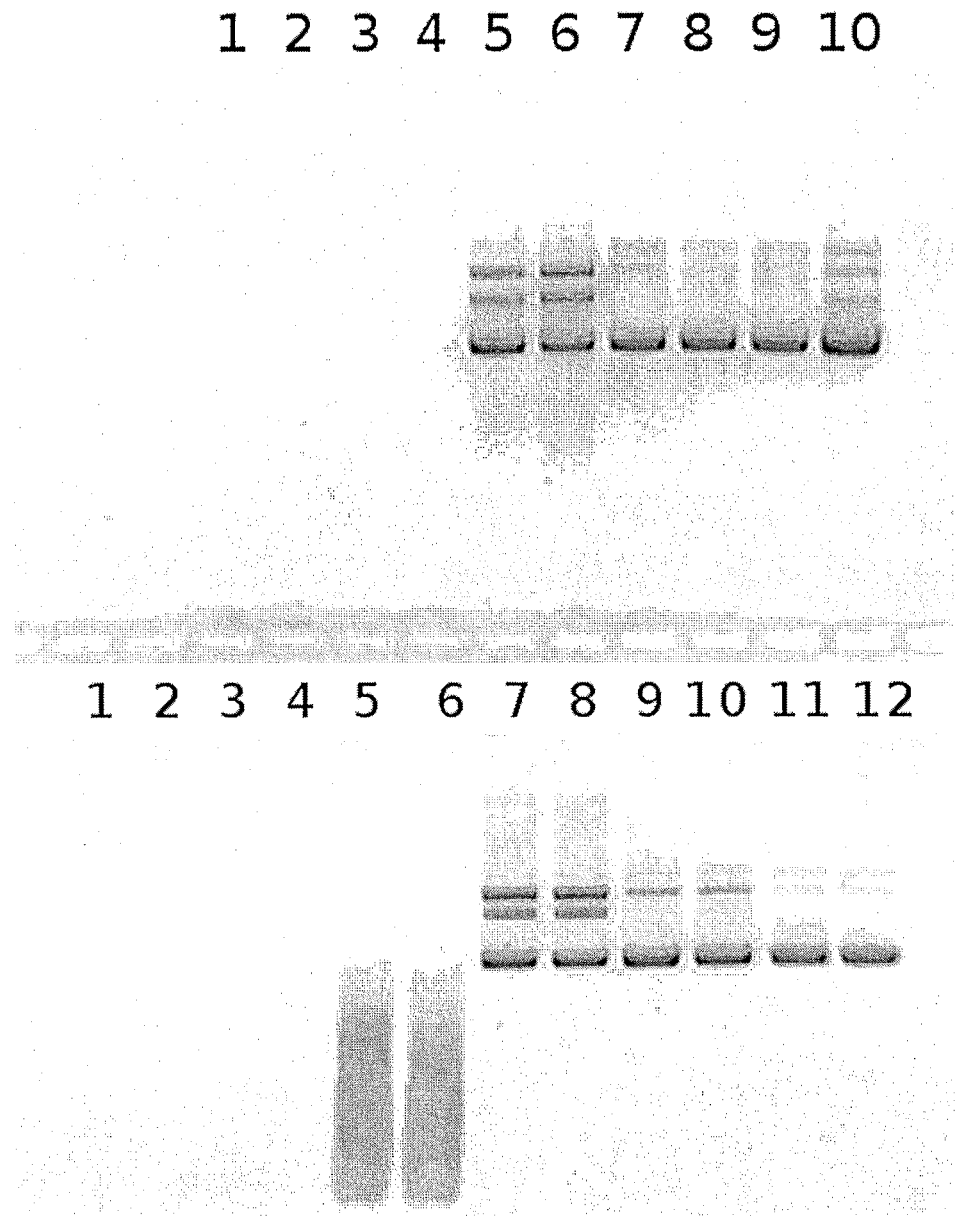
FIG. 1 shows complete DNase I removal by synergistic action of CN-silica and dicarboxylic acid in Protein Removal Reagent.

FIG. 1 shows complete DNase I removal by synergistic action of CN-silica and dicarboxylic acid in Protein Removal Reagent. Upper half: 1 unit DNase I in 20 µl of 1× Reaction Buffer with $MgCl_2$ was treated with 2 µl Protein Removal Reagent prepared by suspending CN-silica either in pure water (lanes 5, 6) or in buffer containing Na-adipate (lanes 7, 8) or Na-suberate (lanes 9, 10). For comparison, aliquots of the same reaction mixture had been treated with the same volumes of Na-adipate (lanes 1,2) or Na-suberate (lanes 3, 4) buffer without CN-silica. Two independent reactions were performed for each sample. After centrifugation 20 µl supernatant was transferred to a fresh tube and 1 µg pUC19 DNA was added to each tube and incubated for two h at 37° C. to test for residual DNase I activity. Reactions were analyzed on an agarose gel followed by gel staining with ethidium bromide. Lower half: DNase I were added to 1 µg of pUC19 DNA in 20 µl of 1× Reaction Buffer with $MgCl_2$ and incubated for two h at 37° C. to test the dependence of DNA degradation on DNase I units at the conditions of the experiment. Two independent reactions were performed for each DNase I amount: 1 u (lanes 1, 2), $10^{-2}$ u (lanes 3, 4), $10^{-4}$ u (lanes 5, 6), $10^{-6}$ u (lanes 7, 8), $10^{-7}$ u (lanes 9, 10) and no DNase I control (lanes 11, 12).

As shown in FIG. 1, dicarboxylic acid salts alone had no influence on DNase I activity as the pUC 19 DNA was fully degraded in these samples. There was only slight increase of linear DNA in samples treated with derivatized silica suspended in water, indicating that residual DNase I activity was lower by about five orders of magnitude compared to initial DNase I activity in the sample. Inclusion of adipate or suberate buffer in PRR formulation decreased residual DNase I level left in sample after treatment with PRR by one to two orders of magnitude further as indicated by undetectable DNase I activity in these samples.

EXAMPLE 2

PRR Composition: Performance of PRR Buffer Components

Several versions of PRR were prepared by suspending cyanopropyl derivatized silica in buffers containing salts of various dicarboxylic acids. All dicarboxylic acids have been used as sodium salts at pH 5.0, and cyanopropyl silica has been used as an adsorbent. Each PRR was tested for protein removal efficacy from solution using DNase I as a model enzyme.

Two µl of various PRR were used to remove 2 U of DNase I from 20 µl 1× Reaction Buffer with $MgCl_2$ followed by residual DNase I activity testing in supernatant with pUC 19 DNA, as described in the previous example.

Figure 2:
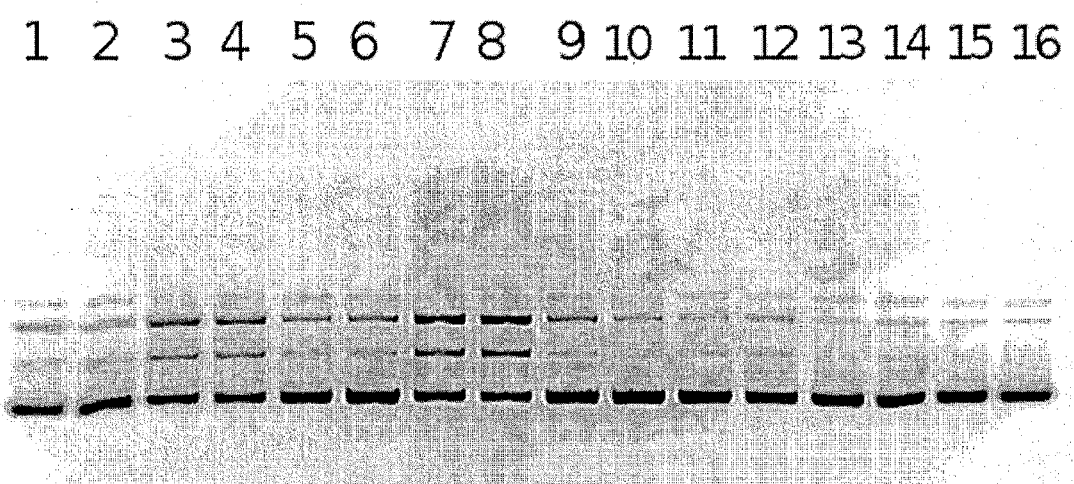
FIG. 2 shows examination of various dicarboxylic acids in combination with CN-silica for DNase I removal.

FIG. 2 shows examination of various dicarboxylic acids in combination with CN-silica for DNase I removal. 50% suspension of CN-silica in buffer of dicarboxylic acid (2 µl) was used for removal of DNase I (2 unit in 20 µl of 1× Reaction Buffer with $MgCl_2$). After centrifugation 20 µl supernatant was transferred to a fresh tube and 1 µg pUC19 DNA was added and incubated for two h at 37° C. to test for residual DNase I activity. Reactions were analyzed on an agarose gel and stained with ethidium bromide. Two independent reactions were performed for each dicarboxylic acid tested: succinate (lanes 1, 2), iminodiacetate (lanes 3, 4), glutarate (lanes 5, 6), glutamate (lanes 7, 8), adipate (lanes 9, 10), pimelate (lanes 11, 12), suberate (lanes 13, 14). Control of supercoiled pUC 19 DNA was loaded in lanes 15 and 16.

Results presented in FIG. 2 show that all tested salts of dicarboxylic acids are suitable for PRR preparation. The longer the methylene chain of aliphatic dicarboxylic acids, the better performance of the PRR, with the exception of very short-chain acids such as succinate and oxalate (data not shown). The latter exception may be explained by the general inhibitory power of short dicarboxy acids on many enzymes, illustrated by the number of enzymes inhibited by each dicarboxylic acid referenced in the BRENDA database (http://www.brenda-enzymes.org), therefore they are less suitable as PRR buffer components:

| Number of $CH_2$ groups between carboxylates | Dicarboxylic acid | Number of inhibited enzymes |
| --- | --- | --- |
| 0 | oxalic | 119 |
| 1 | malonic | 63 |
| 2 | succinic | 115 |
| 3 | glutaric | 25 |
| 4 | adipic | 10 |
| 5 | pimelic | 3 |
| 6 | suberic | 0 |

Some other organic acids that showed satisfactory performance in the capacity of PRR buffer component have no practical utility within the scope of the disclosed invention as they are known as strong inhibitors of many enzymes, e.g., aurintricarboxylic acid (21 enzyme inhibited), or citric acid (203 enzymes inhibited).

Better performance of longer aliphatic molecules is consistent with the presumption that dipole structure of aliphatic dicarboxylic acids in solution enables their action as ion-pairing agents and thus facilitates interactions between sterically isolated functional groups on protein surfaces and those on adsorbent surfaces. Experimental data also demonstrate that introduction of charged functional groups decrease the performance of buffer component. This is evident from the behavior of two pairs of acids: succinic vs iminodiacetic (two methylenes), and glutaric vs glutamic (2-aminoglutaric, three methylenes). In both cases nitrogen-containing group decreased the hydrophobicity of methylene chain, and the molecule acquires purely zwitterionic structure devoid of hydrophobic face and thus cannot longer act as an ion-pairing reagent.

EXAMPLE 3

Irreversibility of PRR Action

Types of protein interaction with PRR was tested using DNase I and E. coli RNase I enzymes as models. Reaction mixtures containing either 1 U DNase I in 20 µL 1× Reaction Buffer with $MgCl_2$ or 20 U RNase I in 20 µL 1× FastDigest® Buffer were treated with 2 µL or 1 µL of PRR, respectively. Both supernatant and pellet after centrifugation were saved.

Supernatants were complemented with 1/10 volume of corresponding 10× enzyme reaction buffer to reestablish original reaction conditions, while pellets were re-suspended in the original reaction volumes of 1× corresponding enzyme reaction buffers.

In case the enzymes were inhibited by soluble components of PRR, e.g., by complexation of cofactor metal ions, the addition of reaction buffer components would reconstitute reaction conditions needed for enzyme reactivation and activity. This effect, if present, could be potentially dangerous for downstream applications. In case the protein binding by CN-silica was somewhat reversible the released amounts of enzymes could be recovered after some period of time. This effect could also be potentially dangerous if there was delay before centrifugation or/and supernatant transfer or occasionally some silica particles are transferred together with the supernatant to a fresh tube.

Supernatants and re-suspended pellets were incubated at room temperature generally favoring protein refolding and renaturation. After fixed periods of time, aliquots were taken from the samples and tested for enzymatic activities. DNase I activity was assayed with pUC 19 DNA as described in Example 1. RNase I activity was measured by sample incubation with [$^3$H]-RNA and subsequent counting of radioactivity released into acid-soluble fraction. RNase I samples were supplemented with 200 µg [$^3$H]-RNA and incubated for 30 min at 37° C. Subsequently two volumes of cold 10% TCA were added and samples were kept for 15 min in an ice bath, followed by ten min centrifugation at 14,000 rpm. Supernatant was transferred to a scintillation vial containing 5 ml scintillation cocktail Rotiszint® eco plus (Roth) and radioactivity was counted with a Beckman LS 1801 scintillation counter. Recovered RNase I activity was recalculated in % of RNase I activity in control sample without any treatment.

Figure 3:
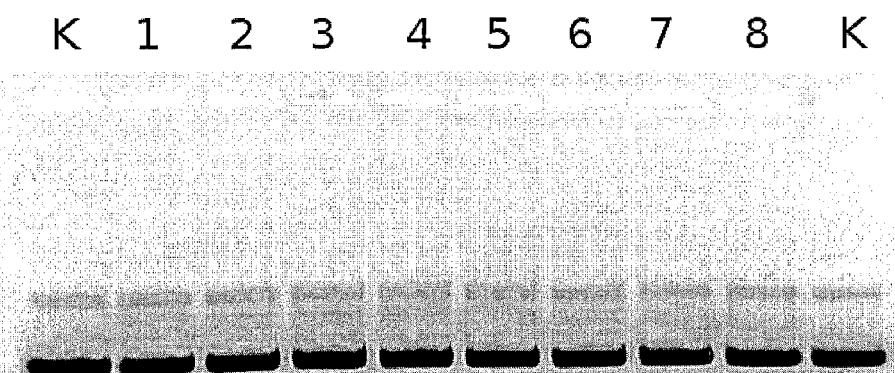
FIG. 3 demonstrates irreversible adsorption of DNase I by Protein Removal Reagent.

DNase I assay results are shown in FIG. 3. RNase I assay results are shown in FIG. 4.

FIG. 3 demonstrates irreversible adsorption of DNase I by Protein Removal Reagent. One unit of DNase I in 20 µl 1× Reaction Buffer with $MgCl_2$ was treated with 2 µl PRR. After centrifugation the supernatant was complemented with 1/10 volume of 10× Reaction Buffer with $MgCl_2$, while the pellet was re-suspended in 20 μl 1× Reaction Buffer with MgCl$_2$. Enzyme was allowed for to renaturate and/or dissociate from adsorbent for 3 min, 1.1 h, 3 h, or 93 h (lanes 2, 4, 6, 8 for supernatant samples and lanes 3, 5, 7, 9 for pellet samples respectively) at room temperature. To evaluate recovered DNase I activity 1 μg pUC19 DNA was added and incubated for two h at 37° C. All reactions and control of intact pUC 19 DNA (lane 1) were analyzed on an agarose gel and stained with ethidium bromide.

Figure 4:
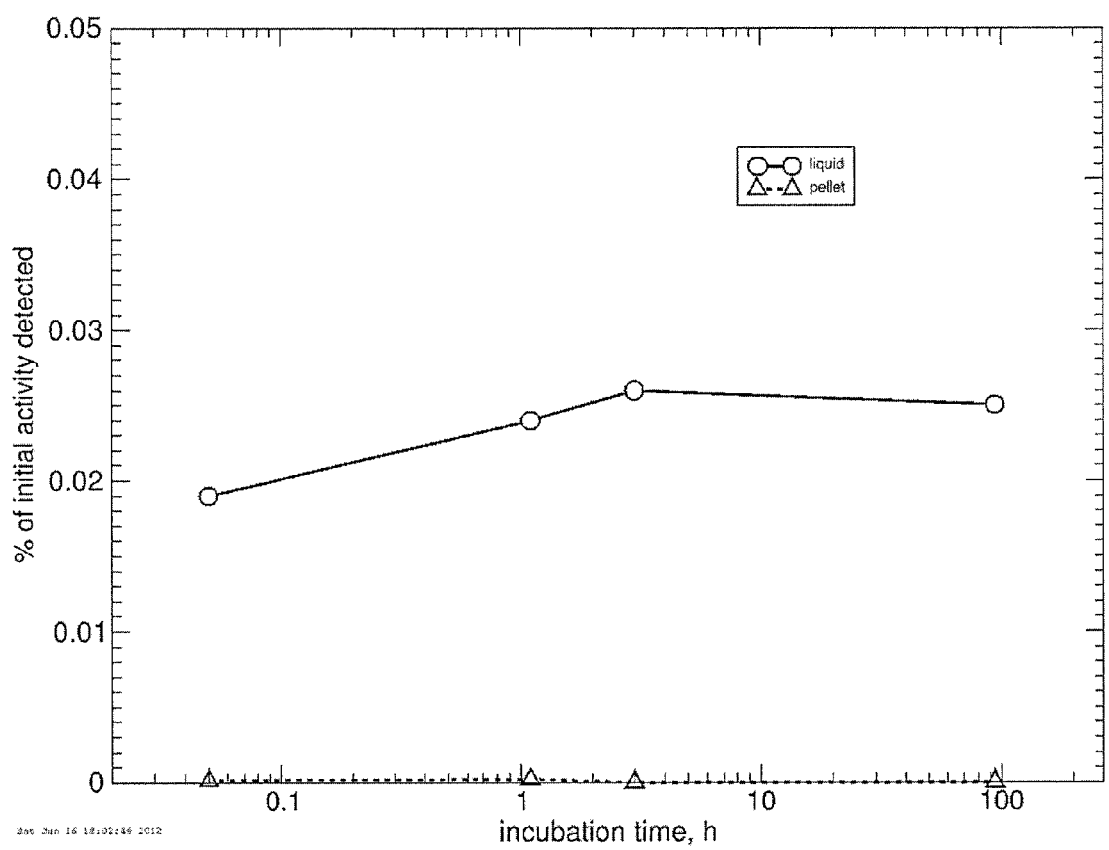
FIG. 4 demonstrates irreversible adsorption of RNase I by Protein Removal Reagent.

FIG. 4 demonstrates RNase I by Protein Removal Reagent. Twenty U of RNase I in 20 μL FastDigest® buffer was treated with 1 μL PRR. After centrifugation the supernatant was complemented with 1/10 volume 10× FastDigest® buffer, while the pellet was re-suspended in 20 μl of 1× FastDigest® buffer. After incubation for 3 min, 1.1 h, 3 h, or 93 h at room temperature, 200 μg [$^3$H]-RNA was added and incubated for 30 min. After precipitation with TCA radioactivity released into acid-soluble fraction was counted. Recovered RNase I activity was recalculated in % of RNase I activity without treatment with PRR. Triangles: residual RNase I activity extracted from adsorbent with 1× FastDigest® reaction buffer. Circles: RNase I activity left in supernatant.

In both cases only traces of activity of tested enzymes were detected. Because no increase of residual enzyme activity was detected in the supernatant after prolonged incubation, it was inferred that no enzyme reactivation occurred, i.e., the protein was fully removed from solution. Even if the silica microspheres containing the adsorbed enzyme were suspended in reaction buffer resembling the situation if silica with adsorbed protein is not removed by centrifugation, no residual or reactivatable enzymatic activity was detected after prolonged incubation at conditions favoring reactivation. This indicated that the protein binding by PRR was fully irreversible.

EXAMPLE 4

Efficiency of PRR in Removal of Various Proteins

Universal action of several PRR versions in removing various proteins from reaction mixtures was tested using enzymes that, in a molecular biology research workflow, are most commonly removed from reaction mixtures before taking their substrate into the new subsequent reaction.

PRR was prepared by suspending cyanopropyl derivatized silica (50% slurry) either in pure water or in buffer containing dicarboxylic acid salt (Na-adipate or Na-suberate) at pH 5.0.
Functional Removal of Restriction Enzymes Restriction enzymes are often used in manipulations with DNA and, as a rule, they must always be inactivated after DNA digestion. This is usually achieved by enzyme denaturation at high temperatures. However, many restriction enzymes, both thermophilic and mesophilic, withstand heat treatment, so tedious protocols of DNA purification by organic solvents must be applied. Functional removal of restriction enzymes from reaction mixtures by PRR is illustrated using FastDigest® PstI restriction enzyme as an example; several other enzymes have been tested as well. Although mesophilic, this particular enzyme is not inactivated by heat.

The experiment was performed as follows: 20 μL reaction mixture containing 1× FastDigest® reaction buffer and 1 FDU of enzyme was prepared. Two μL PRR reagents, in water or Na-suberate, were added. The resulting mixtures were mixed by vortex mixing, the silica was pelleted (spun down), and supernatants were saved into fresh tubes. One μg λ phage DNA was added to all reaction mixtures. Control samples containing only water or suberate buffer (without silica) were incubated for five min, while PRR treated samples were incubated for two h at 37° C. Results were analyzed by DNA electrophoresis.

Figure 5:
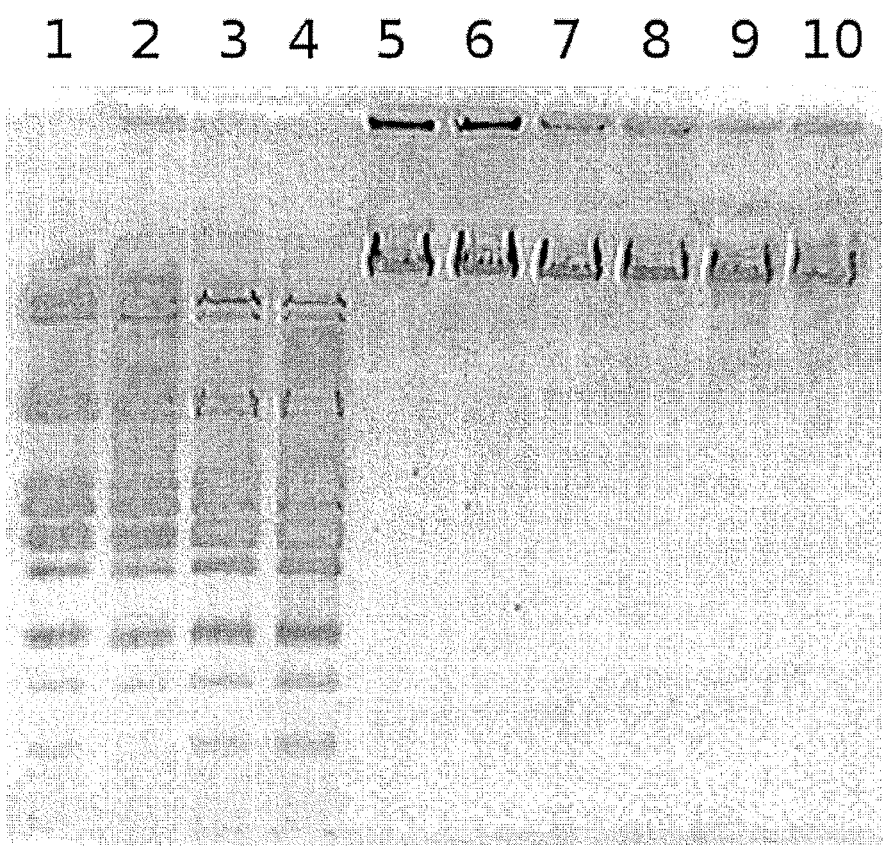
FIG. 5 shows removal of FastDigest® PstI restriction enzyme from reaction mixture by Protein Removal Reagent.

FIG. 5 shows removal of FastDigest® PstI restriction enzyme from a reaction mixture by Protein Removal Reagent. One μl FastDigest® PstI in 20 μL 1× FastDigest® buffer was treated with 2 μL CN-silica suspension in water (lanes 5, 6), or in 100 mM Na-suberate (lanes 7, 8). After centrifugation supernatants were supplemented with 1 μg λ phage DNA and incubated for two h at 37° C. to test residual restriction enzyme activity. Control samples were prepared by adding only water (lanes 1, 2) or Na-suberate buffer (lanes 3, 4) to Pst I reaction mixture and were incubated for five min at 37° C. All reactions were prepared in duplicate and with intact λ phage DNA control (lanes 9, 10) were separated by electrophoresis in agarose gel with ethidium bromide.

Results in FIG. 5 show that 2 μL PRR was able to completely remove 1 FDU of restriction enzyme PstI. Other FD restrictions enzymes tested, EcoRV, BglII, were successfully removed as well.
Functional Removal of Polymerases Functional removal of polymerases by PRR was tested using *Thermus aquaticus* DNA polymerase. This enzyme, being thermophilic, is impossible to inactivate by heat.

The experiment was performed as follows: 50 μL reaction mixture containing 1× Taq Buffer with KCl (10 mM Tris-HCl (pH 8.8), 50 mM KCl, 0.08% Nonidet P40, 1.5 mM MgCl$_2$) and 1.25 U enzyme was prepared. Five μL PRR reagents, in water or Na-adipate or Na-suberate, were added, mixtures were vortexed, silica was pelleted (spun down) and supernatants were saved in fresh tubes. Control samples containing only water or dicarboxylic acid buffer (without silica) were prepared. Polymerase activity was determined in all samples. Five μL supernatant or control sample was combined with 45 μL mix containing 67 mM Tris-HCl (pH 8.8), 6.7 mM MgCl$_2$, 1 mM DTT, 50 mM NaCl, 0.1 mg/mL BSA, 0.25 mg/mL activated salmon sperm DNA, 0.2 mM dNTP, and 0.37 MBq/mL tritium-labeled dTTP. Reactions were incubated for 30 min at 70° C. Forth μl reaction was spotted on DE-81 paper disc. Paper discs were washed four times for ten min with 7.5% Na$_2$HPO$_4$×10 H$_2$O, rinsed twice with water and once with acetone, dried, placed into a scintillation vial containing 5 ml of scintillation cocktail Betaplate Scint (Perkin Elmer), and counted for radioactivity with Beckman LS 1801 scintillation counter. Residual polymerase activity (%) was calculated with respect to polymerase activity in control sample with water (without silica).

Figure 6:
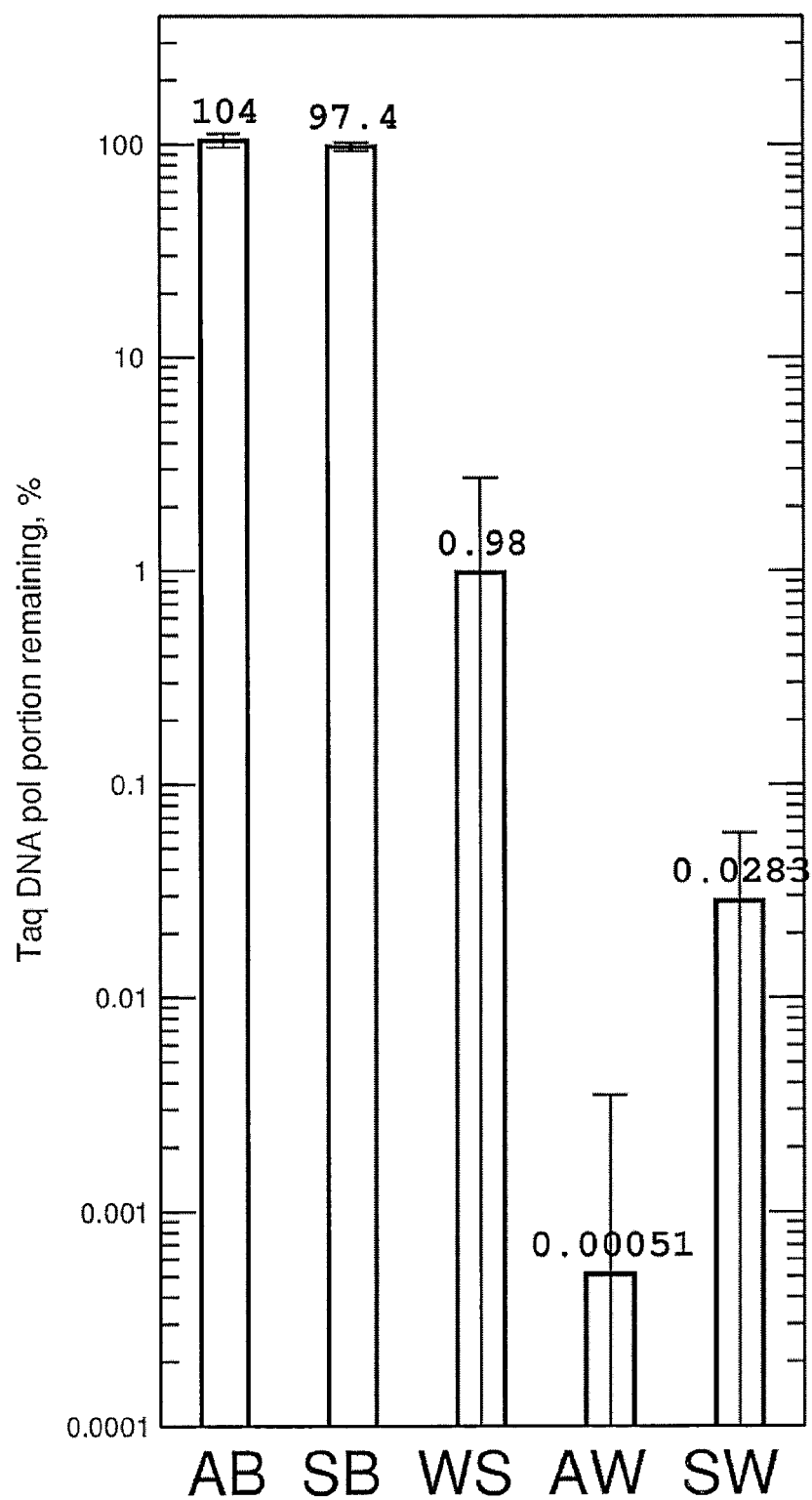
FIG. 6 shows removal of Taq DNA polymerase from reaction mixture by Protein Removal Reagent.
Figure 7:
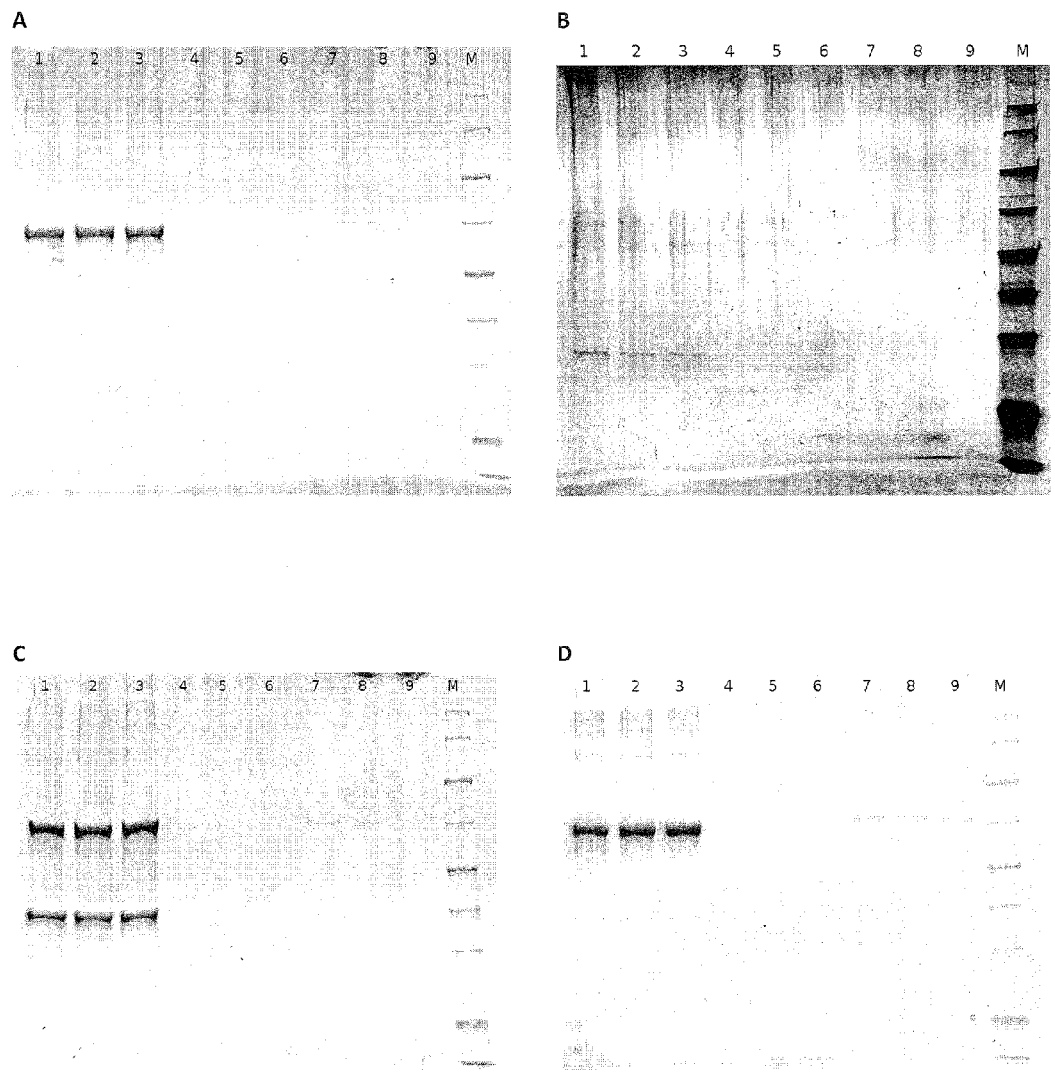
FIGS. 7A-F show SDS-PAGE visualisation of proteins extraction by Protein Removal Reagent.
Figure 7:
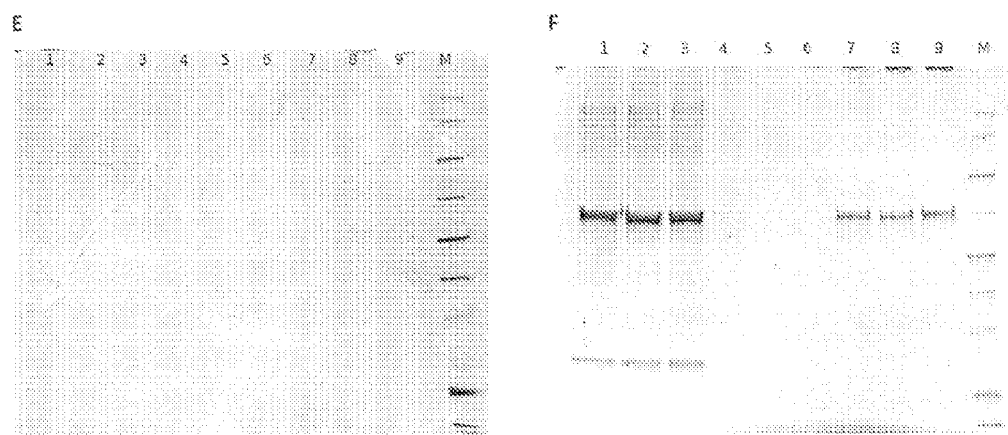

FIG. 6 shows removal of Taq DNA polymerase from reaction mixture by Protein Removal Reagent. 1.25 U Taq DNA polymerase in 50 μL of 1× Taq Buffer with KCl was treated with 5 μL of CN-suspension in water (column WS) or in 100 mM Na-adipate (column AW) or Na-suberate (column SW). After centrifugation 5 μl of supernatants was added to 45 μl of polymerase activity measurement mixture (67 mM Tris-HCl (pH 8.8), 6.7 mM MgCl$_2$, 1 mM DTT, 50 mM NaCl, 0.1 mg/mL BSA, 0.25 mg/mL activated salmon sperm DNA, 0.2 mM dNTP, 0.37 MBq/mL [$^3$H]-dTTP) and incubated for 30 min at 70° C. Taq activity was calculated from radioactivity adsorbed on DE-81 filters. Control samples were prepared by addition of only water or 100 mM Na-adipate (column AB) or Na-suberate buffer (column SB) to Taq I reaction mixture and polymerase activity was measured as described above. Residual Taq DNA polymerase activity was recalculated in % of polymerase activity in control sample with water. All displayed results are the mean values of at least three experiments with error bars of one standard deviation.

The results shown in FIG. 6 demonstrated that after treatment with cyanopropyl silica suspension alone in pure water, polymerase activity was reduced by about two orders of magnitude. Enzyme removal with cyanopropyl silica in water was significant; concerted action of cyanopropyl derivatized silica and dicarboxylic acid salt resulted in substantially complete polymerase removal as the measured polymerase activities were lower than the experimental error margins.

Physical Removal of Various Proteins from Reaction Mixtures

Analytical protein electrophoresis demonstrated that the principle of PRR action was based solely on the physical removal of proteins from reaction mixtures. Experiments were performed with a variety of proteins extracted with PRR from their conventional reaction mixtures. Experiments were performed as follows: 20 µL of the reaction mixture containing conventional enzyme reaction buffer and quantity of enzyme usually employed in routine molecular biology procedures were prepared. One-tenth volume of PRR reagent in water or Na-adipate or Na-suberate were added, mixtures were mixed by vortex mixer, silica was pelleted (spun down) and supernatants were saved in fresh tubes. Control samples containing only water or dicarboxylic acid buffer (without silica) were also prepared. Supernatant and control samples were supplemented with 5 µL 4× DualColor™ Protein Loading Buffer containing DTT. Silica precipitates were suspended in 20 µL 1× DualColor™ Protein Loading Buffer containing DTT. All samples were incubated at 100° C. for ten min, analyzed by SDS-PAGE with the gel stained with PageBlue™ Protein Staining Solution or PageSilver™ Silver Staining Kit (Taq polymerase and DNase I gels).

The following proteins were tested in these experiments (quantity of protein in 20 µL reaction mixture): 2 µg bovine serum albumin (~70 kDa) in water, 1 unit DNase I (~30 kDa) in 1× Reaction Buffer with $MgCl_2$, 1 unit FastAP™ alkaline phosphatase (~40 kDa) in 1× FastAP Buffer (BSA included), 1 FDU FastDigest® PstI restriction nuclease (~40 kDa) in 1× FastDigest® Buffer (BSA included), 0.5 u Taq DNA polymerase (~100 kDa) in 1× Taq Buffer with KCl, and 10 units *E. coli* RNase I (~25 kDa) in 1× FastDigest® Buffer (BSA included).

FIGS. 7A-F show SDS-PAGE visualisation of proteins extraction by Protein Removal Reagent. 20 µL of the reaction mixture containing conventional enzyme reaction buffer and quantity of enzyme usually employed in routine molecular biology procedures were prepared and treated with 2 µL of CN-silica suspension in water or in 100 mM Na-adipate or Na-suberate. After centrifugation, supernatants were supplemented with 5 µl of 4× DualColor™ Protein Loading Buffer containing DTT (lanes 4, 5, 6 for CN silica in water, Na-adipate and Na-suberate respectively), while the pellet was re-suspended in 20 µl of 1× DualColor™ Protein Loading Buffer containing DTT (lanes 7, 8, 9 for CN silica in water, Na-adipate and Na-suberate respectively). Control samples were prepared by addition of only water (lane 1) or 100 mM Na-adipate (lane 2) or Na-suberate (lane 3) buffer to enzymes and later supplemented with 5 µl of 4× DualColor™ Protein Loading Buffer containing DTT for electrophoresis. All samples were denatured at 100° C. for 10 min and analyzed by SDS-PAGE and stained with PageBlue™ Protein Staining Solution except DNase I gel (B) and Taq DNA polymerase gel (E) stained with PageSilver™ Silver Staining Kit. PageRuler™ Unstained Broad Range Protein Ladder (Thermo Scientific) was loaded in last M lane: 250, 150, 100, 70, 50, 40, 30, 20, and 15 kDa bands were visible. The following proteins were tested in this experiment: (A) 2 µg of bovine serum albumin, (B) 1 unit of DNase I, (C) 1 unit of FastAP™ alkaline phosphatase, (D) 1 FDU of FastDigest® PstI restriction nuclease, (E) 0.5 u of Taq DNA polymerase and (F) 10 units of *E. coli* RNase I. BSA band (~70 kDa) from reaction buffer along with enzymes was visible in C, D and E gels.

The electrophoresis results were very similar for all proteins tested. The results clearly demonstrated that after treatment with PRR no protein was left in the sample. Even if BSA was present in enzyme reaction buffer (FIG. 7C, FastAP buffer and D, F, FastDigest® Buffer) PRR was able to remove enzyme together with BSA except when cyanopropyl silica suspension in water was used for FastAP™ alkaline phosphatase (FIG. 7C) or RNase I (FIG. 7F) extraction where a faint BSA band was still visible. However dicarboxylic acid salt inclusion in silica suspension enabled physical removal of all tested proteins from reaction mixtures. Detergent included in Taq buffer had no interference for polymerase extraction with all PRR tested. The dicarboxylic acid salt buffers alone had no effect on the physical integrity of tested proteins as these samples are identical to water samples. The protein binding to PRR was so strong that even very aggressive extraction conditions, boiling of suspended silica in sample buffer containing strong detergent SDS, failed to liberate the major portion of the protein adsorbed onto silica.

In summary, the data showed that 2 µL PRR was able to bind irreversibly and remove from reaction about 2 µg protein down to the quantity undetectable by SDS-PAGE. Although cyanopropyl silica microspheres alone physically adsorb protein almost on par with the PRR suspended in the buffer of dicarboxylic acid salt, they were less efficient in removing residual functional activity of enzymes as was shown in the previously described examples, summarized in the table below:

| Enzyme | Enzyme quantity in reaction mixture, U | Volume of reaction mixture*, µL | Residual activity after PRR treatment | | Activity measurement method |
| --- | --- | --- | --- | --- | --- |
| | | | CN-silica in water | CN-silica in dicarboxylic acid buffer | |
| DNase I | 1 | 20 | $<10^{-5}$ u | undetectable | Functional assay—supercoiled plasmid DNA degradation |
| RNase I (*E. coli*) | 20 | 20 | <0.03% | <0.001% | Functional assay with [$_3$H]-RNA-counting of radioactivity released into acid-soluble fraction |

-continued

| Enzyme | Enzyme quantity in reaction mixture, U | Volume of reaction mixture*, μL | Residual activity after PRR treatment | | Activity measurement method |
|---|---|---|---|---|---|
| | | | CN-silica in water | CN-silica in dicarboxylic acid buffer | |
| Phosphatase FastAP ™ | 1 | 20 | — | 0-0.4% | Functional assay—spectrophotometrical detection of p-NPP hydrolysis |
| FastDigest ® EcoRV** | 1 FDU*** | 50 | none | none | Functional assay—λ DNA digestion |
| FastDigest ® PstI | 1 FDU | 50 | none | none | Functional assay—λ DNA digestion |
| FastDigest ® BglII** | 1 FDU | 50 | none | none | Functional assay—λ DNA digestion |
| Taq DNA polymerase | 1.25 | 50 | 1% | <0.03% | Functional assay—incorporation of nucleotides into a polynucleotide fraction (absorbed on DE-81) |

*in all cases 1/10 volume of PRR was added to reaction mixtures for enzyme removal
**results not presented
**FDU—FastDigest units

EXAMPLE 5

Nucleic Acids Yields After PRR Treatment

Many molecular biology research workflows may be described as a consecutive series of reactions, where certain starting nucleic acid acts as a substrate for several subsequent enzymatic reactions. Often the next enzymatic reaction requires removal of the preceding enzyme from the reaction mixture. In such a workflow it is important that methods used for enzyme removal do not have negative effect on the concentration of the nucleic acid remaining in the reaction mixture, i.e., it is desirable that enzyme removal should occur without any concurrent loss of the substrate nucleic acid. The effect of PRR treatment on the concentration of nucleic acid remaining in the reaction mixture was tested using synthetic RNA as a control and DNase I as a protein for removal (FIG. 8).

Figure 8:
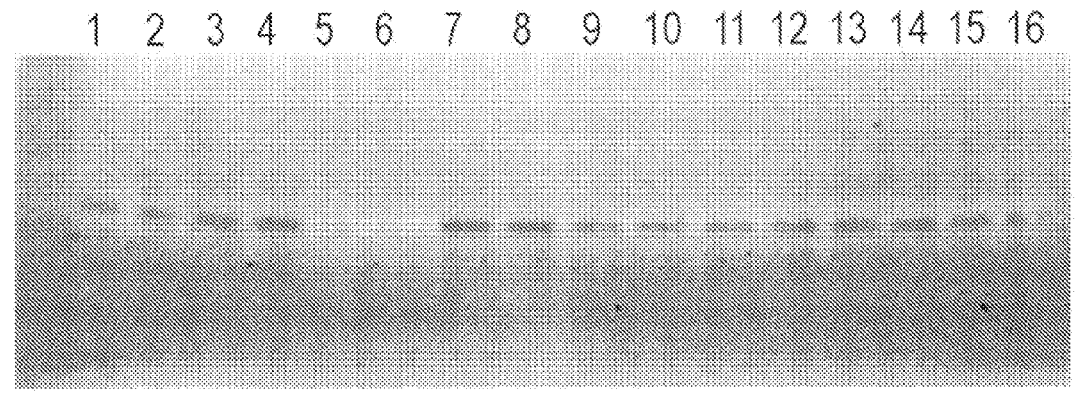
FIG. 8 shows RNA yields after Protein Removal Reagent treatment.

FIG. 8 shows RNA yields after Protein Removal Reagent treatment. Solutions of 100 ng synthetic 2 kb RNA in 20 μL 1× Reaction Buffer with MgCl$_2$ were treated with 4 μL of various PRRs (all reactions were prepared in duplicate) made as CN-silica suspension in different buffers –50 mM adipate, pH 5 (lanes 3, 4), 50 mM suberate, pH 5 (lanes 7, 8), 20 mM suberate, pH 5 (lanes 9, 10), 40 mM suberate with 10 mM ammonium sulfate, pH 5 (lanes 11, 12) and 40 mM non-buffered ammonium sulfate (lanes 13, 14). PRR prepared from phenyl-silica in 50 mM suberate (lanes 3, 4) known to bind nucleic acids was included as a negative control. Supernatants together with untreated RNA (lanes 1, 2, 15, 16) were analyzed by agarose gel electrophoresis for the remaining amount of RNA.

Solutions of 100 ng synthetic 2 kb RNA in 20 μL of 1× Reaction Buffer with MgCl$_2$ were treated with 4 μL of various PRRs which were made as 50% CN-silica suspension in different buffers: 50 mM adipate, pH 5.0, 50 mM suberate, pH 5.0, 20 mM suberate, pH 5.0, 40 mM suberate with 10 mM ammonium sulfate, pH 5.0 and 40 mM non-buffered ammonium sulfate. Supernatants were analyzed by gel electrophoresis (1% agarose in TAE with ethidium bromide) for remaining amount of RNA. It is evident that PRRs based on 50 mM dicarboxylic acids salts buffers did not bind RNA, while RNA retention by PRR increased with decreasing buffer concentrations and slightly increased with increased overall ionic strength. Phenyl derivatized silica known to bind nucleic acids was included for comparison as negative control.

EXAMPLE 6

PRR Treatment did not Interfere with Downstream Reactions (RT-QPCR)

One of the most frequently performed procedures in molecular biology is DNA synthesis from small RNA quantities present in samples of various nature. Typically, this procedure is executed as a consecutive set of reactions following RNA purification, including DNase I treatment, reverse transcription, and qPCR where the residual DNase I must be removed prior to reverse transcription. It is important that DNase I removal procedures and reagents used in this process have no negative impact on nucleic acid integrity and yield during reverse transcription and, as no additional purification is performed after RT, during the qPCR step.

qPCR is a very sensitive test for evaluation of nucleic acid yield after PRR treatment. The RT-qPCR procedure may be carried out in a quantitative fashion and nucleic acid yield may be measured in a broad range of concentrations starting from minute quantities of the initial RNA material.

The experiment was performed as follows: 10-fold serial dilutions from 100 ng to 1 pg of HeLa total RNA were treated with 1 U of DNase I in 20 μl 1× Reaction Buffer with MgCl$_2$ for 30 min at 37° C. and then the DNase I was removed with 2 μl of PRR. Four μl supernatant was used for cDNA generation with the Maxima™ First Strand cDNA Synthesis Kit and GAPDH (glyceraldehyde-3-phosphate dehydrogenase) cDNA was detected in subsequent qPCR with the Maxima™ SYBR Green qPCR Master Mix (2×), ROX Solution provided. Untreated RNA dilutions in 1× Reaction Buffer with MgCl$_2$ were used in RT-qPCR as controls.

Figure 9:
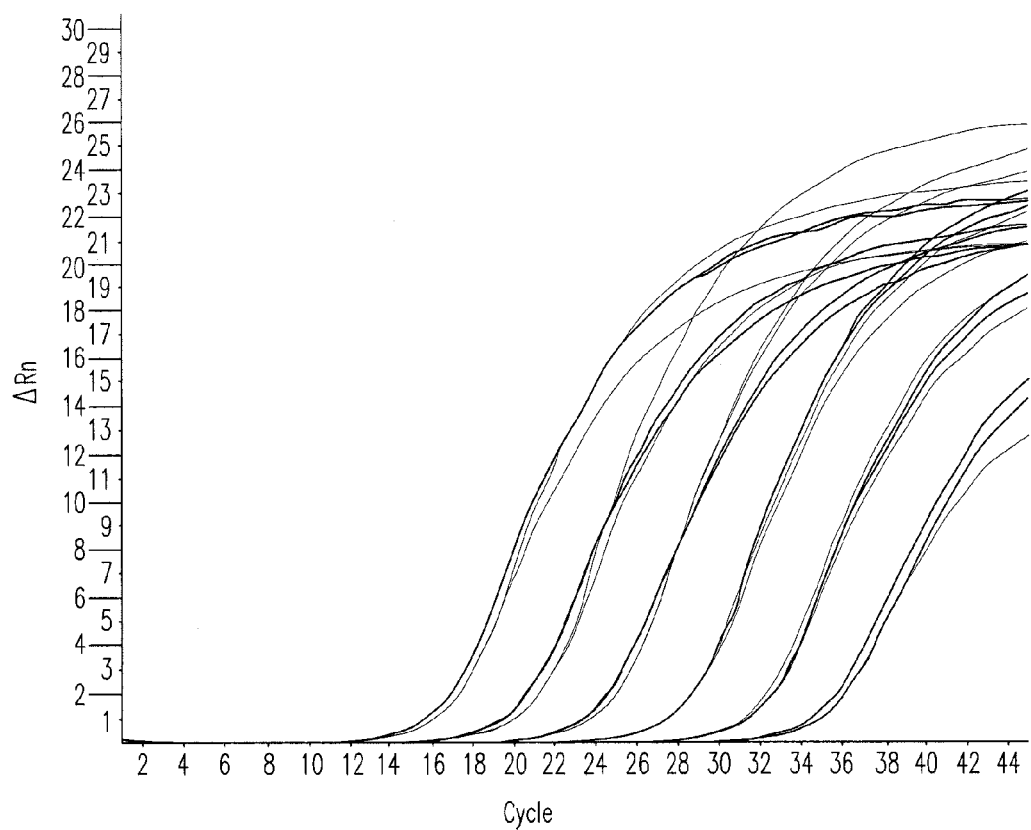
FIG. 9 shows compatibility of DNase I and Protein Removal Reagent Treated Total RNA with Real-Time RT-PCR.

FIG. 9 shows that DNase I and Protein Removal Reagent treated total RNA was compatible with Real time PCR (RT- PCR). Ten-fold serial dilutions from 100 ng to 10 pg (curves from left to right respectively) of HeLa total RNA were treated with 1 U DNase I in 20 µl 1× Reaction Buffer with $MgCl_2$ for 30 min at 37° C. and then the DNase I was removed with 2 µl of PRR. Four µl supernatant was used for cDNA generation with the Maxima™ First Strand cDNA Synthesis Kit, and GAPDH cDNA was detected in subsequent qPCR with the Maxima™ SYBR Green qPCR Master Mix (2×), ROX Solution provided (dark grey curves). Untreated RNA dilutions in 1× Reaction Buffer with $MgCl_2$ were used in RT-qPCR as controls (light grey curves).

Results in FIG. 9 demonstrated that PRR treated RNA was compatible with RT-qPCR and PRR did not extract any RNA, as PRR treatment had no negative effect on RNA yields even at the lowest quantity of RNA used in the experiment.

EXAMPLE 7

Comparison of PRR Efficiency with Commercially Available Analogs

PRR efficiency was tested using pancreatic DNase I as a model enzyme for removal efficacy from a solution containing RNA. PRR efficiency was compared with heat inactivation and the following commercial analogs:
  i) Ambion® TURBO DNA-free™ Kit (Invitrogen, Inc.), used per the manufacturer's recommendations: 2 units of TURBO DNase were removed using 2 µL of DNase removal reagent from the kit
  ii) RTS DNase™ Kit (MoBio Laboratories, Inc.), used per the manufacturer's recommendations: 4 units of DNase were removed using 2 µL of DNase removal reagent from the kit
  iii) DNase I (Stratagene) and StrataClean Resin (Stratagene), 10 units DNase I were removed using StrataClean resin in three successive extraction rounds per the manufacturer's recommendations
  iv) recombinant DNase I (Takara Bio Group) removed using QuickClean™ Enzyme Removal Resin (Clontech, part of Takara Bio Group), 1 unit Recombinant DNase I was removed using QuickClean™ Enzyme Removal Resin in three successive extraction rounds per the manufacturer's recommendations.

Primary reaction mixtures were prepared as follows: 20 µL of solution containing 1 µg RNA (200 b long) and 0.1 µg DNA (HindIII fragments of λ phage DNA) in appropriate DNase I reaction buffer had been supplemented with 1 unit of Thermo Scientific DNase I in PRR test and heat inactivation experiments, or with various other DNases as described above.

After 30 min incubation at 37° C., Thermo Scientific DNase I was captured by adding 2 µL of PRR. Heat inactivated samples supplemented with 2 µL of 50 mM EDTA and heated at 65° C. for 10 min. Other DNases were removed using corresponding removal agents recommended by DNase supplier (or available from the same supplier in the case of standalone DNase) as described above.

All samples were mixed thoroughly and centrifuged at 2400 rpm for 30 sec. Final supernatants were saved in another set of tubes. All reactions were performed in duplicate and 2 µL of water was added to one replicate and 2 µL of corresponding 10× DNase buffer concentrates was added to another replicate to reconstitute DNase reaction conditions designated as renaturation controls. Renaturation controls were included to assess completeness of enzyme removal by ruling out possible inhibitory effects of divalent metal depletion by removal with DNase/protein removing resins or by making complexes with buffer components of resins.

Figure 10:
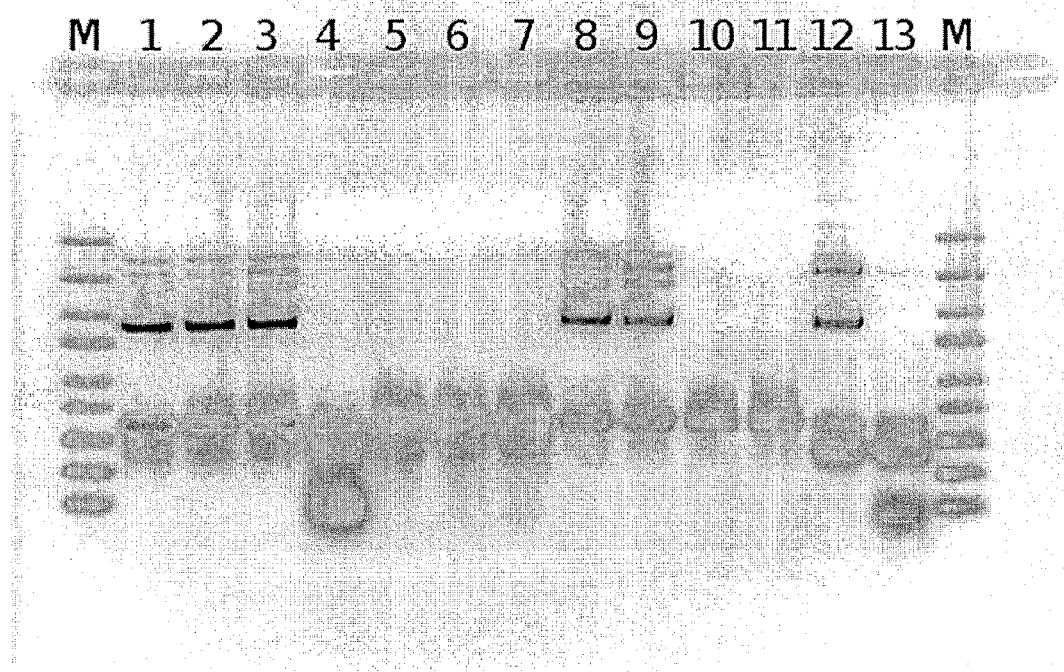
FIG. 10 shows efficiency of DNase I removal by Protein Removal Reagent compared to commercially available analogs.

Subsequently, 2 µL of solution containing 1 µg supercoiled pUC19 plasmid were added to each sample to provide a substrate for remaining DNase I left unbound and samples were incubated for two h at 37° C. (secondary reaction mixtures). All samples had been analyzed electrophoretically in 1% agarose gel in TAE buffer with the gel stained with ethidium bromide to visualize DNA (FIG. 10).

RNA was treated with DNase and then the DNase was removed by following the procedure for routine DNA removal as described. RNA samples contaminated with DNA were prepared by mixing 1 µg RNA (200 b long) with 0.1 µg DNA (HindIII fragments of λ phage DNA) in 20 µL volume. The RNA sample was incubated for 30 min at 37° C. with 1 unit DNase I (Thermo Scientific) in 1× Reaction Buffer with $MgCl_2$ to degrade DNA, and 2 µl of PRR (CN-silica in 50 mM Na-adipate) was used to remove DNase I from the sample. The samples of commercial kits or resins were treated with corresponding DNase and then the DNase was removed per the manufacturer's recommendations. The thermo-inactivated sample was incubated for 30 min at 37° C. with 1 unit of DNase I (Thermo Scientific) in 1× Reaction Buffer with $MgCl_2$ and after that was supplemented with 2 µL of 50 mM EDTA and heated at 65° C. for ten min to inactivate DNase I. All samples were prepared in duplicates. After centrifugation 2 µL of water was added to the supernatant of one replicate and 2 µl of corresponding 10× DNase buffer to another replicate. Subsequently, 2 µL of solution containing 1 µg supercoiled form of pUC19 plasmid was added to each sample to provide a substrate for remaining DNase I and samples were incubated for two h at 37° C. All samples and pUC 19 DNA control were analyzed electrophoretically. Lanes M—GeneRuler™ Express DNA Ladder, 100-5000 bp; Lane 1—supercoiled plasmid pUC19 DNA control; lanes 2, 3—samples treated with DNase I (Thermo Scientific) and PRR without and with extra addition of Reaction Buffer with $MgCl_2$ respectively; lanes 4, 5—samples treated with Ambion®TURBO DNA-free™ Kit (Life Technologies) without and with extra addition of TURBO DNase I Buffer respectively; lanes 6, 7—samples treated with RTS DNase™ Kit (MoBio Laboratories) without and with extra addition of RTS DNase Buffer respectively; lanes 8, 9—samples treated with DNase I (Stratagene) and StrataClean Resin (Stratagene) in three extraction cycles without and with extra addition of DNase I Buffer respectively; lanes 10, 11—samples treated with Recombinant DNase I (TAKARA BIO Inc.) and QuickClean™ Enzyme Removal Resin (Clontech) in three extraction cycles without and with extra addition of DNase I Buffer (TAKARA BIO) respectively; lanes 12, 13—thermo-inactivated samples without and with extra addition of Reaction Buffer with $MgCl_2$, respectively.

DNase removal by PRR treatment was more complete than that by commercial analogs or by DNase I thermoinactivation. The PRR action uses the irreversible denaturation and fixation of inactive protein on the solid phase instead of chelation of stabilizing enzyme cofactor metal ions. Supplementation of purified supernatant with divalent metal ions did not restore enzymatic activity.

Although StrataClean resin shows similar final efficiency of DNase extraction as PRR, StrataClean requires three successive extraction stages, while PRR needs only single extraction round to achieve complete DNase I removal. This repeated extraction inadvertently results in significantly reduced RNA yield. StrataClean is believed to use a resin which has surface phenol groups.

While EDTA/heat inactivation results in complete DNase I inactivation, enzyme is not physically removed from reaction mixture. Upon reactivating conditions after addition of 1×

Reaction Buffer with MgCl$_2$ DNase I had reactivated to a degree sufficient for complete digestion of DNA during secondary reaction. Heat treatment could also damage RNA, particularly if EDTA-unbound divalent metal ions are left.

Both TURBO® DNA-free™ DNase Treatment and Removal Reagents kit and RTS DNase™ Kit showed incomplete removal of their respective DNases. Although such DNase removal level may be sufficient for certain applications, it may be detrimental for some more sensitive downstream procedures; QuickClean™ resin showed significantly lower ability to remove DNase even when three successive extraction rounds were deployed.

What is claimed is:

1. A composition for removing protein contaminants from a solution containing a target nucleic acid, the composition comprising
   (i) a polyacid comprising a polycarboxylic acid, a polyphosphonic acid, or a polycarboxylate or polyphosphonate salt;
   (ii) a solid phase comprising a functionalized silica surface; and
   (iii) the solution containing the target nucleic acid and protein contaminants.

2. The composition of claim 1 where the solid phase comprises silica.

3. The composition of claim 1 where the solid phase comprises particles.

4. The composition of claim 3 where the particles are substantially spherical and have a diameter in the range of from 3 μm to 15 μm.

5. The composition of claim 3 where the particles have pores with a diameter of from 10 nm to 100 nm.

6. The composition of claim 1 where the functionalized silica bears anionic or neutral substituent groups that are (i) polar, other than phenol, and/or (ii) comprise a $C_1$ to $C_3$ alkyl chain.

7. The composition of claim 6 where the substituent groups are selected from cyanoalkyl groups (CN—(CH$_2$)$_n$—) where n is an integer of at least 3;
   short chain alkyl groups (CH$_3$—(CH$_2$)$_m$—) where m is 0, 1, or 2;
   sulfoalkyl groups (HSO$_3$—(CH$_2$)$_l$—) where l is an integer in the range 2 to 6;
   alkanoyl groups (CH$_3$—(CH$_3$)$_p$—CO—O—) where p is 0, 1, or 2;
   a diol ((OH)$_2$—CH—(CH$_2$)$_r$—) or hydroxyl OH—(CH$_2$)$_r$— where r is zero or an integer in the range 1 to 5, or mixed diol CH$_2$OH—CHOH—(CH$_2$)$_r$—;
   a cyclohexyldiol C$_6$H$_3$(OH)$_2$—(CH$_2$)$_t$—;
   alkylhalides Hal-(CH$_2$)$_t$—, tosylhalides SO$_2$Hal-C$_6$H$_4$—(CH$_2$)$_t$—, tosyl SO$_3$H—C$_6$H$_4$—(CH$_2$)$_t$—, or alkylphenylhalides Hal-(CH$_2$)$_u$—C$_6$H$_4$—(CH$_2$)$_t$— where Hal is halogen, t is 2, 3, or 4, and u is 0, 1, or 2.

8. The composition of claim 7 where the substituent groups are cyanopropyl groups.

9. The composition of claim 1 where the surface of the solid phase further comprises silane groups of general formula —O—Si—R$_3$ where each R is independently $C_1$-$C_3$ alkyl.

10. The composition of claim 9 where each R is methyl.

11. The composition of claim 1 where the polyacid comprises a polycarboxylic acid.

12. The composition of claim 11 where the polycarboxylic acid comprises a dicarboxylic acid.

13. The composition of claim 12 where the dicarboxylic acid is aliphatic.

14. The composition of claim 12 where the dicarboxylic acid is unsubstituted.

15. The composition of claim 14 where the dicarboxylic acid is COOH—(CH$_2$)$_q$—COON where q is from 4 to 6.

16. The composition of claim 15 where the dicarboxylic acid is adipic acid.

17. The composition of claim 1 where the polyacid is present at a concentration up to 200 mM.

18. The composition of claim 1 buffered at a pH from 4.5 to 7.0.

19. The composition of claim 1 where the protein contaminants are irreversibly adsorbed onto the solid phase.

20. The composition of claim 1 where the polyacid facilitates attraction between the protein contaminants and the solid phase.

21. A method for removing protein contaminants from a solution containing target nucleic acid, the method comprising contacting a solution containing target nucleic acid and protein contaminants with (i) a polyacid comprising a polycarboxylic acid, a polyphosphonic acid, or a polycarboxylate or polyphosphonate salt; and (ii) a solid phase comprising a functionalized silica surface, forming the composition of claim 1, under conditions that the protein contaminants bind to the solid phase to form a treated solution; and separating the treated solution from the solid phase.

* * * * *